United States Patent [19]

Olson

[11] Patent Number: 4,852,185
[45] Date of Patent: Aug. 1, 1989

[54] PROTECTIVE FACE SHIELD

[76] Inventor: David V. Olson, 929 Medical Arts Bldg., Minneapolis, Minn. 55402

[21] Appl. No.: 106,866

[22] Filed: Oct. 13, 1987

[51] Int. Cl.$^4$ .............................................. A61F 9/06
[52] U.S. Cl. ............................................................ 2/9
[58] Field of Search ........................................ 2/9, 436

[56] References Cited

U.S. PATENT DOCUMENTS

| | | | |
|---|---|---|---|
| 797,293 | 8/1905 | Lang et al. | 2/12 |
| 3,395,406 | 8/1968 | Smith | 2/436 |
| 3,686,690 | 8/1972 | Webb | 2/9 |
| 4,435,852 | 3/1984 | Nesler | 2/436 |
| 4,701,965 | 10/1987 | Landis | 2/9 |

FOREIGN PATENT DOCUMENTS

| | | | |
|---|---|---|---|
| 0655814 | 1/1938 | Fed. Rep. of Germany | 2/9 |
| 0688227 | 1/1940 | Fed. Rep. of Germany | 2/9 |

Primary Examiner—Werner H. Schroeder
Assistant Examiner—Jeanette E. Chapman
Attorney, Agent, or Firm—Burd, Bartz & Gutenkauf

[57] ABSTRACT

A protective face shield intended primarily for use by health care professionals to reduce the transmission of infectious diseases carried by viral and bacterial emissions from the noses and throats of afflicted patients. The protective face shield comprises a generally flat crescent-shaped semi-rigid body member adapted to engage the forehead of the wearer. It includes a resilient head-engaging means to attach the body member to the wearer's head. The body member supports a depending semi-rigid face-covering transparent sheet which forms a barrier to the transmission of disease causing organisms. Vents are provided in the body member to prevent fogging of the shield.

10 Claims, 1 Drawing Sheet

U.S. Patent      Aug. 1, 1989      4,852,185
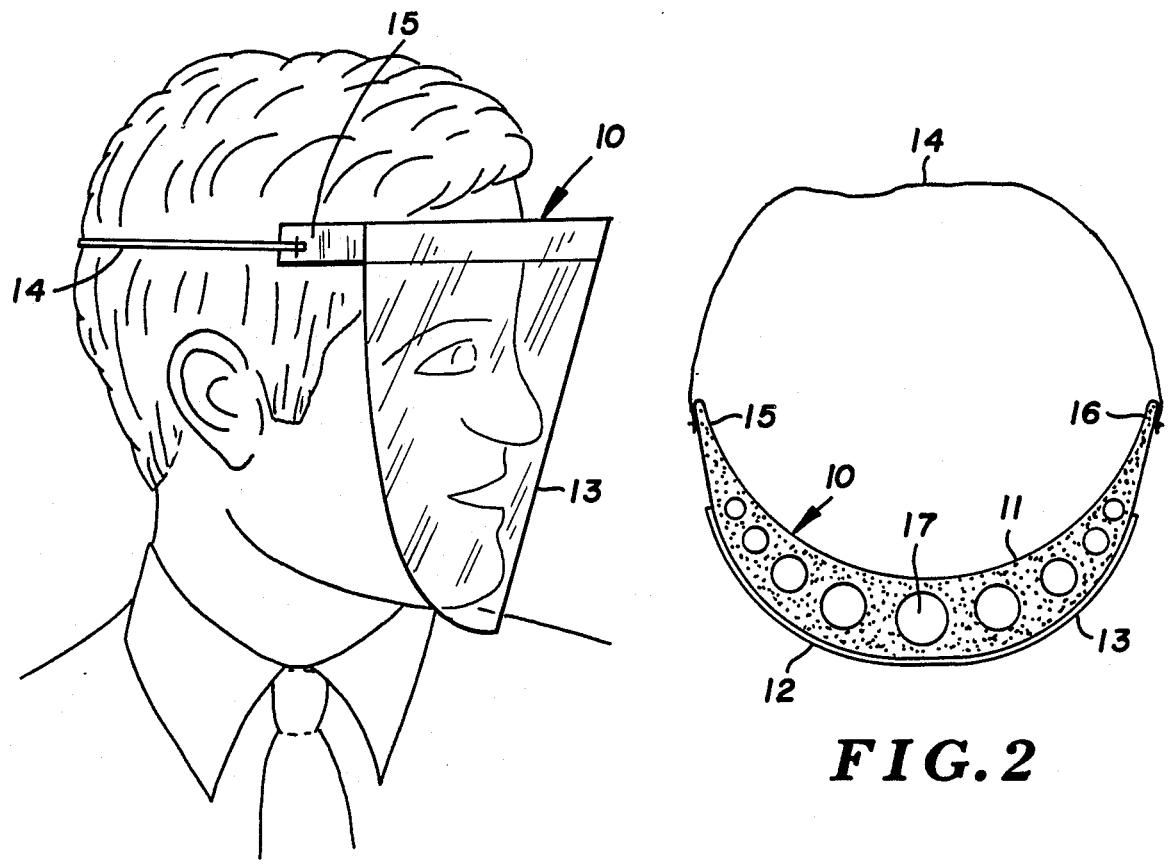
FIG.1
FIG.2
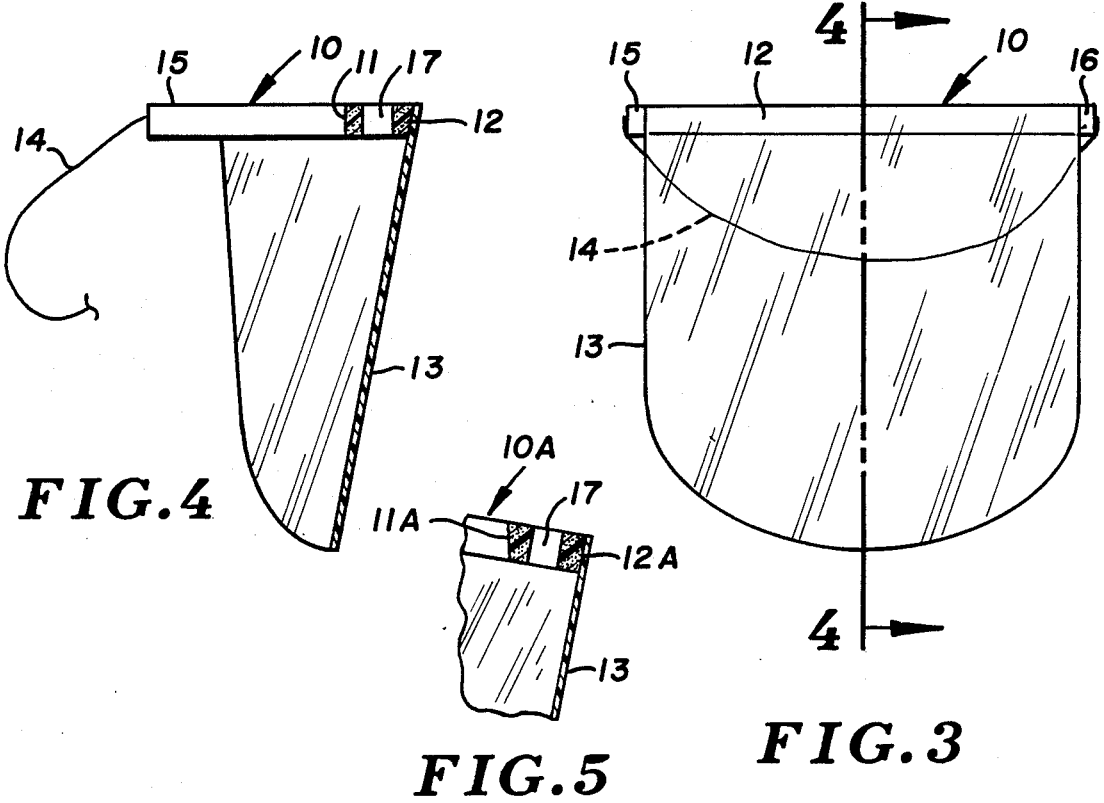
FIG.4
FIG.5
FIG.3

PROTECTIVE FACE SHIELD

BACKGROUND OF THE INVENTION

1. Field of the Invention

This invention is directed to a protective device for shielding the face of its wearer from flying particles, splashed liquids, aerosol emissions, and the like. The protective face shield according to the present invention is intended primarily as a simple inexpensive disposable device for use by health care professionals against the transmission of viral and bacterial diseases such as upper respiratory infections, acquired immune deficiency syndrome (AIDS), herpes simplex, hepatitis B, tuberculosis, and the like. Dentists, dental technicians, rhinologists, pharyngologists, and similar health care specialists who are exposed to nasal and/or oral emissions and secretions are especially susceptible. Although intended primarily for use by such health care professionals, the protective face shield of the present invention may be used to protect the face and eyes from metallic particles, rock chips, dust, paint splatters, and the like, generated in the course of carrying out a myriad of household and industrial tasks.

2. The Prior Art

Relatively expensive heavy duty face shields are available in the market for such persons as welders, bicyclists and motorcyclists, and the like. Adaptations of these shields are available in the health care field but they are relatively bulky and expensive. Instead, most health care professionals use face masks in combination with safety glasses or goggles.

SUMMARY OF THE INVENTION

It is the principal object of the present invention to provide a simple lightweight inexpensive disposable face shield which may be discarded after use. Broadly stated, the protective face shield according to the present invention comprises a generally flat crescent-shaped semi-rigid body member having a forehead-engaging rearward edge, and a semi-rigid face-covering transparent sheet secured to the forward edge of that body to extend over the wearer's face. A resilient head-engaging means is attached to the body member for securing the shield to a wearer's head. To prevent fogging, vertical vent means are provided through the body member.

BRIEF DESCRIPTION OF THE DRAWINGS

The invention is illustrated in the accompanying drawings in which corresponding parts are identified by the same numerals and in which:

FIG. 1 is a right side elevation showing the protective face shield in use on the head of a person to be protected;

FIG. 2 is a top plan view of the face shield;

FIG. 3 is a front elevation thereof;

FIG. 4 is a section on the line 4—4 of FIG. 3 and in the direction of the arrows; and FIG. 5 is a similar fragmentary sectional view showing an alternative form of body member cross section.

DETAILED DESCRIPTION OF THE PREFERRED EMBODIMENT

Referring now to the drawings, the protective face shield of the present invention comprises a flat generally crescent-shaped body member indicated generally at 10. The body member 10 has an inner or rearward forehead-engaging arcuate edge 11 and an outer or forward arcuate edge 12. A semi-rigid face-covering transparent sheet 13 is fixedly secured to the forward edge 12 of the body member 10. Preferably transparent sheet 13 extends downwardly from the body by a distance at least sufficient to reach the chin of a wearer of the shield. However, where the primary intended use of the shield is protection of the eyes, the transparent sheet may be shorter. The width of the transparent sheet is sufficient that it substantially encloses the face of a wearer.

In use, the rearward edge of the body member engages the forehead of the wearer and is held in place by means of a resilient head-engaging band 14 secured to the ends 15 and 16 of the body member 10. The head engaging band may be in the form of an adjustable flexible buckled strap, or tieable cords or tapes. Preferably, however, the head-engaging means is in the form of an elastic cord or tape which is self-adjusting and permits easy donning and removal of the face shield. The maximum width of the body member 10 at its mid-portion is sufficient to extend the transparent sheet 13 so as to be free of the tip of the nose of the wearer, and eyeglasses if worn.

Because the face shield substantially encloses the face of the wearer, in order to avoid the accumulation of breath vapors which would fog the transparent sheet, vent means in the form of a plurality of generally vertical holes 17 are provided in the body member. Vent holes 17 are preferably of varying diameters diminishing from the mid-point of the body member 10 toward the ends 15 and 16. Besides performing a venting function, holes 17 impart added resilience to the body member and provide convenient finger holds for aiding in putting the face shield on and taking if off. In addition, the vent holes 17 allow overhead light to pass through.

Transparent sheet 13 may extend substantially vertically and parallel relative to the face of the wearer. Preferably, however, the transparent member is canted inwardly toward the chin of the wearer, for maximum protection. This may be accomplished in either of two ways. As seen in FIG. 4, inner forehead-engaging edge 11 is substantially perpendicular relative to the topmost surface of the body member and the forward edge 12 is beveled inwardly from that topmost surface. Alternatively, as seen in FIG. 5, the rearward edge 11A may be beveled outwardly or forwardly from the topmost surface of the body member 10A and the forward edge 12A is substantially perpendicular to that topmost surface.

The body member 10 is preferably composed of lightweight synthetic resinous plastic foam such as polystyrene, polyethylene, polyurethane, vinyls, or the like. The transparent sheet material may be composed, for example, of transparent polypropylene, polyethylene, polyvinyl chloride, or the like. The transparent member is preferably cut from flat sheet material and formed by securing adhesively or otherwise to the forward edge of the body member. The arcuate form of the semi-rigid transparent material imparts some rigidity to the face covering portion for maximum protection. Although not bound by specific dimensions, by way of illustration, the maximum width of the body member at its mid-section may be about ½ to 2½ inches. The thickness may be about ½ to 1 inch. The transparent sheet may be about 8 to 10 inches wide and about 7 to 9 inches deep, and preferably has an arcuate lower edge, as illustrated. The beveled edges of the body member preferably are about 5° to 15° from perpendicular.

The protective face shield according to the present invention is of simple construction and is composed of inexpensive materials which are readily available. Because of this, the face shield may be regarded as disposable after use in the examination and/or treatment of each individual patient. It is lightweight and comfortable to wear and is easily donned and removed.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A protective face shield comprising:
   (A) a generally flat crescent-shaped semi-rigid body member composed of synthetic resinous plastic foam having a forehead-engaging rearward edge,
   (B) resilient head-engaging means attached to said body member for securing the body member to a wearer's head,
   (C) vertical vent means through said body member, and
   (D) a semi-rigid face-covering transparent sheet fixedly secured to the forward edge of said body member and depending therefrom.

2. A face shield according to claim 1 wherein the forward edge of said body member is beveled inwardly from the topmost surface.

3. A face shield according to claim 1 wherein the rearward edge of said body member is beveled outwardly from the topmost surface.

4. A face shield according to claim 1 wherein said vent means comprise a plurality of generally vertical holes through said body member, at least one of said holes being of a size to function as a finger hold to facilitate putting the shield on and taking it off.

5. A face shield according to claim 4 wherein said holes are of varying diameters diminishing from the mid-point of said body member toward its ends.

6. A face shield according to claim 1 wherein said head-engaging means comprises an elastic band, the ends of which are attached to the ends of said body member.

7. A face shield according to claim 1 wherein said transparent sheet is composed of synthetic resinous plastic sheet material.

8. A protective face shield comprising:
   (A) a generally flat crescent-shaped semi-rigid body member composed of synthetic resinous plastic foam and having a forehead-engaging rearward edge,
   (B) an elastic head-engaging band connected at its ends to the ends of the body member for securing the body member to a wearer's head,
   (C) a plurality of generally vertical vent holes through said body member, at least one of said holes being of a size to function as a finger hold to facilitate putting the shield on and taking it off, said holes being of varying diameters diminishing from the mid-point of said body member toward its ends, and
   (D) a semi-rigid face-covering transparent synthetic resinous plastic sheet fixedly secured to the forward edges of said body member and depending therefrom.

9. A face shield according to claim 8 wherein the forward edge of said body member is beveled inwardly from the topmost surface.

10. A face shield according to claim 8 wherein the rearward edge of said body member is beveled outwardly from the topmost surface.

* * * * *